(12) United States Patent
Keler et al.

(10) Patent No.: US 8,318,165 B2
(45) Date of Patent: Nov. 27, 2012

(54) ANTIBODIES AGAINST HUMAN MELANOMA-ASSOCIATED CHONDROITIN SULPHATE PROTEOGLYCAN (MCSP)

(75) Inventors: Tibor Keler, Ottsville, PA (US); Laura A. Vitale, Doylestown, PA (US); Lizhen He, Allentown, PA (US)

(73) Assignee: Celldex Therapeutics Inc., Needham, MA (US)

( * ) Notice: Subject to any disclaimer, the term of this patent is extended or adjusted under 35 U.S.C. 154(b) by 406 days.

(21) Appl. No.: 12/439,912

(22) PCT Filed: Sep. 10, 2007

(86) PCT No.: PCT/US2007/019717
§ 371 (c)(1),
(2), (4) Date: May 13, 2010

(87) PCT Pub. No.: WO2008/030625
PCT Pub. Date: Mar. 13, 2008

(65) Prior Publication Data
US 2010/0303816 A1 Dec. 2, 2010

Related U.S. Application Data

(60) Provisional application No. 60/843,323, filed on Sep. 8, 2006.

(51) Int. Cl.
*A61K 39/395* (2006.01)
(52) U.S. Cl. ............... 424/138.1; 424/139.1; 424/141.1; 530/387.1; 530/387.7
(58) Field of Classification Search .................. None
See application file for complete search history.

(56) References Cited

U.S. PATENT DOCUMENTS

| 2001/0048922 A1 | 12/2001 | Romet-Lemonne et al. | |
|---|---|---|---|
| 2004/0141913 A1 | 7/2004 | Young et al. | |
| 2004/0197328 A1 * | 10/2004 | Young et al. | 424/141.1 |

FOREIGN PATENT DOCUMENTS

| WO | 97/13855 | * | 4/1997 |
|---|---|---|---|
| WO | WO-2006/032127 A1 | | 3/2006 |

OTHER PUBLICATIONS

Bumol, T.F. et al., "Monoclonal antibody and an antibody-toxin conjugate to a cell surface proteoglycan of melanoma cells suppress in vivo tumor growth," *Proc. Natl. Acad. Sci. USA*, vol. 80:529-533 (1983).
Campoli, Michael R. et al., "Human High Molecular Weight-Melanoma-Associated Antigen (HMW-MAA): A Melanoma Cell Surface Chondroitin Sulfate Proteoglycan (MSCP) with Biological and Clinical Significance," *Critical Reviews in Immunology*, vol. 24(4):267-296 (2004).
Fanger, Michael W. et al., "Production and Use of Anti-FcR Bispecific Antibodies," *Immunomethods*, vol. 4:72-81 (1994).
Ghose, Tarun et al., "Regression of human melanoma xenografts in nude mice injected with mexotrexate linked to monoclonal antibody 225.28 to human high molecular weight-melanoma associated antigen," *Cancer Immunology Immunotherapy*, vol. 34:90-96 (1991).
Giacomini, Patrizio et al., "Analysis of the interaction between a human high molecular weight melanoma-associated antigen and the monoclonal antibodies to three distinct antigenic determinants," *The Journal of Immunology*, vol. 135(1):696-702 (1985).
Imai, K. et al., "ADCC of Cultured Human Melanoma Cells: Analysis with Monoclonal Antibodies to Human Melanoma-associated Antigens," *Scand. J. Immunol.*, vol. 14:369-377 (1981).
Neri, Dario et al., "Recombinant Anti-Human Melanoma Antibodies Are Versatile Molecules," *J. Invest. Dermatol.*, vol. 107:164-170 (1996).
Schulz, Gregor et al., "Monoclonal antibody-directed effector cells selectively lyse human melanoma cells in vitro and in vivo," *Proc. Natl. Acad. Sci. USA*, vol. 80:5407-8411 (1983).
Schulz, Gregor et al., "Eradication of Established Human Melanoma Tumors in Nude Mice by Antibody-directed Effector Cells," *J. Exp. Med.*, vol. 161:1315-1325 (1985).
Wang, Baiyang et al., "Human single-chain Fv Immunoconjugates targeted to a melanoma-associated chondroitin sulfate proteoglycan mediate specific lysis of human melanoma cells by natural killer cells and complement," *Proc. Natl. Acad. Sci. USA*, vol. 96:1627-1632 (1999).
Internatonal Search Report and Written Opinion for Application No. PCT/US2007/019717, dated May 27, 2008.

* cited by examiner

*Primary Examiner* — Sheela J Huff
(74) *Attorney, Agent, or Firm* — Nelson Mullins Riley & Scarborough LLP; Jane E. Remillard, Esq.; Jill Gorny Sloper, Esq.

(57) ABSTRACT

The present invention provides isolated antibodies (e.g., humanized or human antibodies) that bind to the membrane-proximal domain (MP) of human Melanoma-Associated Chondroitin Sulphate Proteoglycan (MCSP), and are capable of mediating cytolysis of a cell expressing MCSP in the presence of human effector cells or complement. Methods of using such antibodies to induce cytolysis (e.g., ADCC or CDCC) of cells expressing MP-MCSP are also provided.

25 Claims, 9 Drawing Sheets

Human MCSP Amino Acid Sequence

```
   1 mqsgrgpplp apglalaltl tmlarlasaa sffgenhlev pvataltdid lqlqfstsqp
  61 eallllaagp adhlllqlys grlqvrlvlg qeelrlqtpa etllsdsiph tvvltvvegw
 121 atlsvdgfln assavpgapl evpyglfvgg tgtlglpylr gtsrplrgcl haatlngrsl
 181 lrpltpdvhe gcaeefsasd dvalgfsgph slaafpawgt qdegtleftl ttqsrqapla
 241 fqaggrrgdf iyvdifeghl ravvekgqgt vllhnsvpva dgqphevsvh inahrleisv
 301 dqypthtsnr gvlsyleprg slllggldae asrhlqehrl gltpeatnas llgcmedlsv
 361 ngqrrglrea lltrnmaagc rleeeeyedd ayghyeafst lapeawpame lpepcvpepg
 421 lppvfanftq lltisplvva eggtawlewr hvqptldlme aelrksqvlf svtrgahyge
 481 leldilgaqa rkmftlldvv nrkarfihdg sedtsdqlvl evsvtarvpm psclrrgqty
 541 llpiqvnpvn dpphiifphg slmvilehtq kplgpevfqa ydpdsacegl tfqvlgtssg
 601 lpverrdqpg epatefscre leagslvyvh cggpaqdltf rvsdglqasp patlkvvair
 661 paiqihrstg lrlaqgsamp ilpanlsvet navgqdvsvl frvtgalqfg elqkhstggv
 721 egaewwatqa fhqrdveqgr vrylstdpqh haydtvenla levqvgqeil snlsfpvtiq
 781 ratvwmlrle plhtqntqqe tlttahleat leeagpsppt fhyevvqapr kgnlqlqgtr
 841 lsdgqgftqd diqagrvtyg ataraseave dtfrfrvtap pyfsplytfp ihiggdpdap
 901 vltnvllvvp eggegvlsad hlfvkslnsa sylyevmerp rlgrlawrgt qdkttmvtsf
 961 tnedllrgrl vyqhddsett eddipfvatr qgessgdmaw eevrgvfrva iqpvndhapv
1021 qtisrifhva rggrrllttd dvafsdadsg fadaqlvltr kdllfgsiva vdeptrpiyr
1081 ftqedlrkrr vlfvhsgadr gwiqlqvsdg qhqatallev qasepylrva ngsslvvpqg
1141 gqgtidtavl hldtnldirs gdevhyhvta gprwgqlvra gqpatafsqq dlldgavlys
1201 hngslspedt mafsveagpv htdatlqvti alegplaplk lvrhkkiyvf qgeaaeirrd
1261 qleaaqeavp padivfsvks ppsagylvmv srgaladepp sldpvqsfsq eavdtgrvly
1321 lhsrpeawsd afsldvasgl gaplegvlve levlpaaipl eaqnfsvpeg gsltlappll
1381 rvsgpyfptl lglslqvlep pqhgplqked gpqartlsaf swrmveeqli ryvhdgsetl
1441 tdsfvlmana semdrqshpv aftvtvlpvn dqppilttnt glqmwegata pipaealrst
1501 dgdsgsedlv ytieqpsngr vvlrgapgte vrsftqaqld gglvlfshrg tldggfpfrl
1561 sdgehtspgh ffrvtaqkqv llslkgsqtl tvcpgsvqpl ssqtlrasss agtdpqllly
1621 rvvrgpqlgr lfhaqqdstg ealvnftqae vyagnilyeh emppepfwea hdtlelqlss
1681 ppardvaatl avavsfeaac pqrpshlwkn kglwvpegqr aritvaalda snllasvpsp
1741 qrsehdvlfq vtqfpsrgql lvseeplhag qphflqsqla agqlvyahgg qgtqqdqfhf
1801 rahlqgpaga svagpqtsea faitvrdvne rppqpqasvp lrltrgsrap israqlsvvd
1861 pdsapgeiey evqraphngf lslvggglgp vtrftqadvd sgrlafvang ssvagifqls
1921 msdgaspplp mslavdilps aievqlrapl evpqalgrss lsqqqlrvvs dreepeaayr
1981 liqgpqyghl lvggrptsaf sqfqidqgev vfaftnfsss hdhfrvlala rgvnasavvn
2041 vtvrallhvw aggpwpqgat lrldptvlda gelanrtgsv prfrllegpr hgrvvrvpra
2101 rtepggsqlv eqftqqdled grlglevqrp egrapgpagd sltlelwaqg vppavasldf
2161 atepynaarp ysvallsvpe aarteagkpe sstptgepgp masspepava kqqflsflea
2221 nmfsviipmc lvllllalil pllfylrkrn ktgkhdvqvl takprnglag dtetfrkvep
2281 gqaipltavp gqgpppggqp dpellqfcrt pnpalkngqy wv
```

*FIG. 1*

SEQUENCE LISTING

```
<160> NUMBER OF SEQ ID NOS: 2

<210> SEQ ID NO 1
<211> LENGTH: 2322
<212> TYPE: PRT
<213> ORGANISM: Homo sapiens

<400> SEQUENCE: 1

Met Gln Ser Gly Arg Gly Pro Pro Leu Pro Ala Pro Gly Leu Ala Leu
 1               5                  10                  15

Ala Leu Thr Leu Thr Met Leu Ala Arg Leu Ala Ser Ala Ala Ser Phe
            20                  25                  30

Phe Gly Glu Asn His Leu Glu Val Pro Val Ala Thr Ala Leu Thr Asp
        35                  40                  45

Ile Asp Leu Gln Leu Gln Phe Ser Thr Ser Gln Pro Glu Ala Leu Leu
    50                  55                  60

Leu Leu Ala Ala Gly Pro Ala Asp His Leu Leu Leu Gln Leu Tyr Ser
65                  70                  75                  80

Gly Arg Leu Gln Val Arg Leu Val Leu Gly Gln Glu Glu Leu Arg Leu
                85                  90                  95

Gln Thr Pro Ala Glu Thr Leu Leu Ser Asp Ser Ile Pro His Thr Val
            100                 105                 110

Val Leu Thr Val Val Glu Gly Trp Ala Thr Leu Ser Val Asp Gly Phe
        115                 120                 125

Leu Asn Ala Ser Ser Ala Val Pro Gly Ala Pro Leu Glu Val Pro Tyr
    130                 135                 140

Gly Leu Phe Val Gly Gly Thr Gly Thr Leu Gly Leu Pro Tyr Leu Arg
145                 150                 155                 160

Gly Thr Ser Arg Pro Leu Arg Gly Cys Leu His Ala Ala Thr Leu Asn
```

```
                    165                 170                 175
Gly Arg Ser Leu Leu Arg Pro Leu Thr Pro Asp Val His Glu Gly Cys
            180                 185                 190

Ala Glu Glu Phe Ser Ala Ser Asp Val Ala Leu Gly Phe Ser Gly
            195                 200                 205

Pro His Ser Leu Ala Ala Phe Pro Ala Trp Gly Thr Gln Asp Glu Gly
            210                 215                 220

Thr Leu Glu Phe Thr Leu Thr Thr Gln Ser Arg Gln Ala Pro Leu Ala
225                 230                 235                 240

Phe Gln Ala Gly Gly Arg Arg Gly Asp Phe Ile Tyr Val Asp Ile Phe
                245                 250                 255

Glu Gly His Leu Arg Ala Val Val Glu Lys Gly Gln Gly Thr Val Leu
            260                 265                 270

Leu His Asn Ser Val Pro Val Ala Asp Gly Gln Pro His Glu Val Ser
        275                 280                 285

Val His Ile Asn Ala His Arg Leu Glu Ile Ser Val Asp Gln Tyr Pro
        290                 295                 300

Thr His Thr Ser Asn Arg Gly Val Leu Ser Tyr Leu Glu Pro Arg Gly
305                 310                 315                 320

Ser Leu Leu Leu Gly Gly Leu Asp Ala Glu Ala Ser Arg His Leu Gln
                325                 330                 335

Glu His Arg Leu Gly Leu Thr Pro Glu Ala Thr Asn Ala Ser Leu Leu
            340                 345                 350

Gly Cys Met Glu Asp Leu Ser Val Asn Gly Gln Arg Arg Gly Leu Arg
        355                 360                 365

Glu Ala Leu Leu Thr Arg Asn Met Ala Ala Gly Cys Arg Leu Glu Glu
        370                 375                 380

Glu Glu Tyr Glu Asp Asp Ala Tyr Gly His Tyr Glu Ala Phe Ser Thr
385                 390                 395                 400

Leu Ala Pro Glu Ala Trp Pro Ala Met Glu Leu Pro Glu Pro Cys Val
                405                 410                 415

Pro Glu Pro Gly Leu Pro Pro Val Phe Ala Asn Phe Thr Gln Leu Leu
            420                 425                 430

Thr Ile Ser Pro Leu Val Val Ala Glu Gly Gly Thr Ala Trp Leu Glu
        435                 440                 445

Trp Arg His Val Gln Pro Thr Leu Asp Leu Met Glu Ala Glu Leu Arg
            450                 455                 460

Lys Ser Gln Val Leu Phe Ser Val Thr Arg Gly Ala His Tyr Gly Glu
465                 470                 475                 480

Leu Glu Leu Asp Ile Leu Gly Ala Gln Ala Arg Lys Met Phe Thr Leu
                485                 490                 495

Leu Asp Val Val Asn Arg Lys Ala Arg Phe Ile His Asp Gly Ser Glu
            500                 505                 510

Asp Thr Ser Asp Gln Leu Val Leu Glu Val Ser Val Thr Ala Arg Val
        515                 520                 525

Pro Met Pro Ser Cys Leu Arg Arg Gly Gln Thr Tyr Leu Leu Pro Ile
        530                 535                 540

Gln Val Asn Pro Val Asn Asp Pro Pro His Ile Ile Phe Pro His Gly
545                 550                 555                 560

Ser Leu Met Val Ile Leu Glu His Thr Gln Lys Pro Leu Gly Pro Glu
                565                 570                 575

Val Phe Gln Ala Tyr Asp Pro Asp Ser Ala Cys Glu Gly Leu Thr Phe
            580                 585                 590
```

```
Gln Val Leu Gly Thr Ser Ser Gly Leu Pro Val Glu Arg Arg Asp Gln
            595                 600                 605

Pro Gly Glu Pro Ala Thr Glu Phe Ser Cys Arg Glu Leu Glu Ala Gly
610                 615                 620

Ser Leu Val Tyr Val His Cys Gly Gly Pro Ala Gln Asp Leu Thr Phe
625                 630                 635                 640

Arg Val Ser Asp Gly Leu Gln Ala Ser Pro Ala Thr Leu Lys Val
                645                 650                 655

Val Ala Ile Arg Pro Ala Ile Gln Ile His Arg Ser Thr Gly Leu Arg
            660                 665                 670

Leu Ala Gln Gly Ser Ala Met Pro Ile Leu Pro Ala Asn Leu Ser Val
            675                 680                 685

Glu Thr Asn Ala Val Gly Gln Asp Val Ser Val Leu Phe Arg Val Thr
690                 695                 700

Gly Ala Leu Gln Phe Gly Glu Leu Gln Lys His Ser Thr Gly Gly Val
705                 710                 715                 720

Glu Gly Ala Glu Trp Trp Ala Thr Gln Ala Phe His Gln Arg Asp Val
                725                 730                 735

Glu Gln Gly Arg Val Arg Tyr Leu Ser Thr Asp Pro Gln His His Ala
            740                 745                 750

Tyr Asp Thr Val Glu Asn Leu Ala Leu Glu Val Gln Val Gly Gln Glu
            755                 760                 765

Ile Leu Ser Asn Leu Ser Phe Pro Val Thr Ile Gln Arg Ala Thr Val
770                 775                 780

Trp Met Leu Arg Leu Glu Pro Leu His Thr Gln Asn Thr Gln Gln Glu
785                 790                 795                 800

Thr Leu Thr Thr Ala His Leu Glu Ala Thr Leu Glu Glu Ala Gly Pro
                805                 810                 815

Ser Pro Pro Thr Phe His Tyr Glu Val Gln Ala Pro Arg Lys Gly
            820                 825                 830

Asn Leu Gln Leu Gln Gly Thr Arg Leu Ser Asp Gly Gln Gly Phe Thr
            835                 840                 845

Gln Asp Asp Ile Gln Ala Gly Arg Val Thr Tyr Gly Ala Thr Ala Arg
850                 855                 860

Ala Ser Glu Ala Val Glu Asp Thr Phe Arg Phe Arg Val Thr Ala Pro
865                 870                 875                 880

Pro Tyr Phe Ser Pro Leu Tyr Thr Phe Pro Ile His Ile Gly Gly Asp
                885                 890                 895

Pro Asp Ala Pro Val Leu Thr Asn Val Leu Val Val Pro Glu Gly
            900                 905                 910

Gly Glu Gly Val Leu Ser Ala Asp His Leu Phe Val Lys Ser Leu Asn
            915                 920                 925

Ser Ala Ser Tyr Leu Tyr Glu Val Met Glu Arg Pro Arg Leu Gly Arg
930                 935                 940

Leu Ala Trp Arg Gly Thr Gln Asp Lys Thr Thr Met Val Thr Ser Phe
945                 950                 955                 960

Thr Asn Glu Asp Leu Leu Arg Gly Arg Leu Val Tyr Gln His Asp Asp
                965                 970                 975

Ser Glu Thr Thr Glu Asp Asp Ile Pro Phe Val Ala Thr Arg Gln Gly
            980                 985                 990

Glu Ser Ser Gly Asp Met Ala Trp Glu Glu Val Arg Gly Val Phe Arg
            995                 1000                1005

Val Ala Ile Gln Pro Val Asn Asp His Ala Pro Val Gln Thr Ile Ser
    1010                1015                1020
```

-continued

```
Arg Ile Phe His Val Ala Arg Gly Gly Arg Arg Leu Leu Thr Thr Asp
1025                1030                1035                1040

Asp Val Ala Phe Ser Asp Ala Asp Ser Gly Phe Ala Asp Ala Gln Leu
                1045                1050                1055

Val Leu Thr Arg Lys Asp Leu Leu Phe Gly Ser Ile Val Ala Val Asp
            1060                1065                1070

Glu Pro Thr Arg Pro Ile Tyr Arg Phe Thr Gln Glu Asp Leu Arg Lys
        1075                1080                1085

Arg Arg Val Leu Phe Val His Ser Gly Ala Asp Arg Gly Trp Ile Gln
    1090                1095                1100

Leu Gln Val Ser Asp Gly Gln His Gln Ala Thr Ala Leu Leu Glu Val
1105                1110                1115                1120

Gln Ala Ser Glu Pro Tyr Leu Arg Val Ala Asn Gly Ser Ser Leu Val
                1125                1130                1135

Val Pro Gln Gly Gly Gln Gly Thr Ile Asp Thr Ala Val Leu His Leu
            1140                1145                1150

Asp Thr Asn Leu Asp Ile Arg Ser Gly Asp Glu Val His Tyr His Val
        1155                1160                1165

Thr Ala Gly Pro Arg Trp Gly Gln Leu Val Arg Ala Gly Gln Pro Ala
1170                1175                1180

Thr Ala Phe Ser Gln Gln Asp Leu Leu Asp Gly Ala Val Leu Tyr Ser
1185                1190                1195                1200

His Asn Gly Ser Leu Ser Pro Glu Asp Thr Met Ala Phe Ser Val Glu
                1205                1210                1215

Ala Gly Pro Val His Thr Asp Ala Thr Leu Gln Val Thr Ile Ala Leu
            1220                1225                1230

Glu Gly Pro Leu Ala Pro Leu Lys Leu Val Arg His Lys Lys Ile Tyr
        1235                1240                1245

Val Phe Gln Gly Glu Ala Ala Glu Ile Arg Arg Asp Gln Leu Glu Ala
    1250                1255                1260

Ala Gln Glu Ala Val Pro Pro Ala Asp Ile Val Phe Ser Val Lys Ser
1265                1270                1275                1280

Pro Pro Ser Ala Gly Tyr Leu Val Met Val Ser Arg Gly Ala Leu Ala
                1285                1290                1295

Asp Glu Pro Pro Ser Leu Asp Pro Val Gln Ser Phe Ser Gln Glu Ala
            1300                1305                1310

Val Asp Thr Gly Arg Val Leu Tyr Leu His Ser Arg Pro Glu Ala Trp
        1315                1320                1325

Ser Asp Ala Phe Ser Leu Asp Val Ala Ser Gly Leu Gly Ala Pro Leu
    1330                1335                1340

Glu Gly Val Leu Val Glu Leu Glu Val Leu Pro Ala Ala Ile Pro Leu
1345                1350                1355                1360

Glu Ala Gln Asn Phe Ser Val Pro Glu Gly Gly Ser Leu Thr Leu Ala
                1365                1370                1375

Pro Pro Leu Leu Arg Val Ser Gly Pro Tyr Phe Pro Thr Leu Leu Gly
            1380                1385                1390

Leu Ser Leu Gln Val Leu Glu Pro Pro Gln His Gly Pro Leu Gln Lys
        1395                1400                1405

Glu Asp Gly Pro Gln Ala Arg Thr Leu Ser Ala Phe Ser Trp Arg Met
    1410                1415                1420

Val Glu Glu Gln Leu Ile Arg Tyr Val His Asp Gly Ser Glu Thr Leu
1425                1430                1435                1440

Thr Asp Ser Phe Val Leu Met Ala Asn Ala Ser Glu Met Asp Arg Gln
```

```
                1445                1450                1455
Ser His Pro Val Ala Phe Thr Val Thr Val Leu Pro Val Asn Asp Gln
            1460                1465                1470
Pro Pro Ile Leu Thr Thr Asn Thr Gly Leu Gln Met Trp Glu Gly Ala
        1475                1480                1485
Thr Ala Pro Ile Pro Ala Glu Ala Leu Arg Ser Thr Asp Gly Asp Ser
    1490                1495                1500
Gly Ser Glu Asp Leu Val Tyr Thr Ile Glu Gln Pro Ser Asn Gly Arg
1505                1510                1515                1520
Val Val Leu Arg Gly Ala Pro Gly Thr Glu Val Arg Ser Phe Thr Gln
            1525                1530                1535
Ala Gln Leu Asp Gly Gly Leu Val Leu Phe Ser His Arg Gly Thr Leu
        1540                1545                1550
Asp Gly Gly Phe Pro Phe Arg Leu Ser Asp Gly Glu His Thr Ser Pro
    1555                1560                1565
Gly His Phe Phe Arg Val Thr Ala Gln Lys Gln Val Leu Leu Ser Leu
1570                1575                1580
Lys Gly Ser Gln Thr Leu Thr Val Cys Pro Gly Ser Val Gln Pro Leu
1585                1590                1595                1600
Ser Ser Gln Thr Leu Arg Ala Ser Ser Ser Ala Gly Thr Asp Pro Gln
            1605                1610                1615
Leu Leu Leu Tyr Arg Val Arg Gly Pro Gln Leu Gly Arg Leu Phe
        1620                1625                1630
His Ala Gln Gln Asp Ser Thr Gly Glu Ala Leu Val Asn Phe Thr Gln
    1635                1640                1645
Ala Glu Val Tyr Ala Gly Asn Ile Leu Tyr Glu His Glu Met Pro Pro
1650                1655                1660
Glu Pro Phe Trp Glu Ala His Asp Thr Leu Glu Leu Gln Leu Ser Ser
1665                1670                1675                1680
Pro Pro Ala Arg Asp Val Ala Ala Thr Leu Ala Val Ala Val Ser Phe
            1685                1690                1695
Glu Ala Ala Cys Pro Gln Arg Pro Ser His Leu Trp Lys Asn Lys Gly
        1700                1705                1710
Leu Trp Val Pro Glu Gly Gln Arg Ala Arg Ile Thr Val Ala Ala Leu
    1715                1720                1725
Asp Ala Ser Asn Leu Leu Ala Ser Val Pro Ser Pro Gln Arg Ser Glu
1730                1735                1740
His Asp Val Leu Phe Gln Val Thr Gln Phe Pro Ser Arg Gly Gln Leu
1745                1750                1755                1760
Leu Val Ser Glu Glu Pro Leu His Ala Gly Gln Pro His Phe Leu Gln
            1765                1770                1775
Ser Gln Leu Ala Ala Gly Gln Leu Val Tyr Ala His Gly Gly Gly Gly
        1780                1785                1790
Thr Gln Gln Asp Gly Phe His Phe Arg Ala His Leu Gln Gly Pro Ala
    1795                1800                1805
Gly Ala Ser Val Ala Gly Pro Gln Thr Ser Glu Ala Phe Ala Ile Thr
1810                1815                1820
Val Arg Asp Val Asn Glu Arg Pro Pro Gln Pro Gln Ala Ser Val Pro
1825                1830                1835                1840
Leu Arg Leu Thr Arg Gly Ser Arg Ala Pro Ile Ser Arg Ala Gln Leu
            1845                1850                1855
Ser Val Val Asp Pro Asp Ser Ala Pro Gly Glu Ile Glu Tyr Glu Val
        1860                1865                1870
```

-continued

Gln Arg Ala Pro His Asn Gly Phe Leu Ser Leu Val Gly Gly Leu
    1875                1880                1885

Gly Pro Val Thr Arg Phe Thr Gln Ala Asp Val Asp Ser Gly Arg Leu
1890                1895                1900

Ala Phe Val Ala Asn Gly Ser Ser Val Ala Gly Ile Phe Gln Leu Ser
1905                1910                1915                1920

Met Ser Asp Gly Ala Ser Pro Pro Leu Pro Met Ser Leu Ala Val Asp
            1925                1930                1935

Ile Leu Pro Ser Ala Ile Glu Val Gln Leu Arg Ala Pro Leu Glu Val
        1940                1945                1950

Pro Gln Ala Leu Gly Arg Ser Ser Leu Ser Gln Gln Leu Arg Val
    1955                1960                1965

Val Ser Asp Arg Glu Glu Pro Glu Ala Ala Tyr Arg Leu Ile Gln Gly
    1970                1975                1980

Pro Gln Tyr Gly His Leu Leu Val Gly Gly Arg Pro Thr Ser Ala Phe
1985                1990                1995                2000

Ser Gln Phe Gln Ile Asp Gln Gly Glu Val Val Phe Ala Phe Thr Asn
            2005                2010                2015

Phe Ser Ser Ser His Asp His Phe Arg Val Leu Ala Leu Ala Arg Gly
        2020                2025                2030

Val Asn Ala Ser Ala Val Val Asn Val Thr Val Arg Ala Leu Leu His
    2035                2040                2045

Val Trp Ala Gly Gly Pro Trp Pro Gln Gly Ala Thr Leu Arg Leu Asp
    2050                2055                2060

Pro Thr Val Leu Asp Ala Gly Glu Leu Ala Asn Arg Thr Gly Ser Val
2065                2070                2075                2080

Pro Arg Phe Arg Leu Leu Glu Gly Pro Arg His Gly Arg Val Val Arg
            2085                2090                2095

Val Pro Arg Ala Arg Thr Glu Pro Gly Gly Ser Gln Leu Val Glu Gln
        2100                2105                2110

Phe Thr Gln Gln Asp Leu Glu Asp Gly Arg Leu Gly Leu Glu Val Gly
    2115                2120                2125

Arg Pro Glu Gly Arg Ala Pro Gly Pro Ala Gly Asp Ser Leu Thr Leu
    2130                2135                2140

Glu Leu Trp Ala Gln Gly Val Pro Pro Ala Val Ala Ser Leu Asp Phe
2145                2150                2155                2160

Ala Thr Glu Pro Tyr Asn Ala Ala Arg Pro Tyr Ser Val Ala Leu Leu
            2165                2170                2175

Ser Val Pro Glu Ala Ala Arg Thr Glu Ala Gly Lys Pro Glu Ser Ser
        2180                2185                2190

Thr Pro Thr Gly Glu Pro Gly Pro Met Ala Ser Ser Pro Glu Pro Ala
    2195                2200                2205

Val Ala Lys Gly Gly Phe Leu Ser Phe Leu Glu Ala Asn Met Phe Ser
    2210                2215                2220

Val Ile Ile Pro Met Cys Leu Val Leu Leu Leu Ala Leu Ile Leu
2225                2230                2235                2240

Pro Leu Leu Phe Tyr Leu Arg Lys Arg Asn Lys Thr Gly Lys His Asp
            2245                2250                2255

Val Gln Val Leu Thr Ala Lys Pro Arg Asn Gly Leu Ala Gly Asp Thr
        2260                2265                2270

Glu Thr Phe Arg Lys Val Glu Pro Gly Gln Ala Ile Pro Leu Thr Ala
    2275                2280                2285

Val Pro Gly Gln Gly Pro Pro Gly Gly Gln Pro Asp Pro Glu Leu
    2290                2295                2300

```
Leu Gln Phe Cys Arg Thr Pro Asn Pro Ala Leu Lys Asn Gly Gln Tyr
2305                2310                2315                2320

Trp Val

<210> SEQ ID NO 2
<211> LENGTH: 481
<212> TYPE: PRT
<213> ORGANISM: Homo sapiens

<400> SEQUENCE: 2

Gln Arg Ser Glu His Asp Val Leu Phe Gln Val Thr Gln Phe Pro Ser
  1               5                  10                  15

Arg Gly Gln Leu Leu Val Ser Glu Glu Pro Leu His Ala Gly Gln Pro
             20                  25                  30

His Phe Leu Gln Ser Gln Leu Ala Ala Gly Gln Leu Val Tyr Ala His
         35                  40                  45

Gly Gly Gly Gly Thr Gln Asp Gly Phe His Phe Arg Ala His Leu
     50                  55                  60

Gln Gly Pro Ala Gly Ala Ser Val Ala Gly Pro Gln Thr Ser Glu Ala
 65                  70                  75                  80

Phe Ala Ile Thr Val Arg Asp Val Asn Glu Arg Pro Pro Gln Pro Gln
                 85                  90                  95

Ala Ser Val Pro Leu Arg Leu Thr Arg Gly Ser Arg Ala Pro Ile Ser
            100                 105                 110

Arg Ala Gln Leu Ser Val Val Asp Pro Asp Ser Ala Pro Gly Glu Ile
        115                 120                 125

Glu Tyr Glu Val Gln Arg Ala Pro His Asn Gly Phe Leu Ser Leu Val
130                 135                 140

Gly Gly Gly Leu Gly Pro Val Thr Arg Phe Thr Gln Ala Asp Val Asp
145                 150                 155                 160

Ser Gly Arg Leu Ala Phe Val Ala Asn Gly Ser Ser Val Ala Gly Ile
                165                 170                 175

Phe Gln Leu Ser Met Ser Asp Gly Ala Ser Pro Pro Leu Pro Met Ser
            180                 185                 190

Leu Ala Val Asp Ile Leu Pro Ser Ala Ile Glu Val Gln Leu Arg Ala
        195                 200                 205

Pro Leu Glu Val Pro Gln Ala Leu Gly Arg Ser Ser Leu Ser Gln Gln
    210                 215                 220

Gln Leu Arg Val Ser Asp Arg Glu Glu Pro Glu Ala Ala Tyr Arg
225                 230                 235                 240

Leu Ile Gln Gly Pro Gln Tyr Gly His Leu Leu Val Gly Gly Arg Pro
                245                 250                 255

Thr Ser Ala Phe Ser Gln Phe Gln Ile Asp Gln Gly Glu Val Val Phe
            260                 265                 270

Ala Phe Thr Asn Phe Ser Ser His Asp His Phe Arg Val Leu Ala
        275                 280                 285

Leu Ala Arg Gly Val Asn Ala Ser Ala Val Asn Val Thr Val Arg
    290                 295                 300

Ala Leu Leu His Val Trp Ala Gly Gly Pro Trp Pro Gln Gly Ala Thr
305                 310                 315                 320

Leu Arg Leu Asp Pro Thr Val Leu Asp Ala Gly Glu Leu Ala Asn Arg
                325                 330                 335

Thr Gly Ser Val Pro Arg Phe Arg Leu Leu Glu Gly Pro Arg His Gly
            340                 345                 350
```

-continued

```
Arg Val Val Arg Val Pro Arg Ala Arg Thr Glu Pro Gly Gly Ser Gln
        355                 360                 365

Leu Val Glu Gln Phe Thr Gln Gln Asp Leu Glu Asp Gly Arg Leu Gly
    370                 375                 380

Leu Glu Val Gly Arg Pro Glu Gly Arg Ala Pro Gly Pro Ala Gly Asp
385                 390                 395                 400

Ser Leu Thr Leu Glu Leu Trp Ala Gln Gly Val Pro Pro Ala Val Ala
                405                 410                 415

Ser Leu Asp Phe Ala Thr Glu Pro Tyr Asn Ala Ala Arg Pro Tyr Ser
                420                 425                 430

Val Ala Leu Leu Ser Val Pro Glu Ala Ala Arg Thr Glu Ala Gly Lys
            435                 440                 445

Pro Glu Ser Ser Thr Pro Thr Gly Glu Pro Gly Pro Met Ala Ser Ser
        450                 455                 460

Pro Glu Pro Ala Val Ala Lys Gly Gly Phe Leu Ser Phe Leu Glu Ala
465                 470                 475                 480

Asn
```

ANTIBODIES AGAINST HUMAN MELANOMA-ASSOCIATED CHONDROITIN SULPHATE PROTEOGLYCAN (MCSP)

RELATED APPLICATIONS

This application claims priority to U.S. Provisional Patent Application No. 60/843,323, filed Sep. 8, 2006. The entire contents of the aforementioned application are hereby incorporated herein by reference.

BACKGROUND OF THE INVENTION

Melanoma-Associated Chondroitin Sulfate Proteoglycan (MCSP), also referred to as "high molecular weight melanoma associated antigen" (HMW-MAA), "human melanoma proteoglycan" (HMP), "melanoma-associated proteoglycan antigen" (MPG) and "melanoma chondroitin sulfate proteoglycan" (mel-CSPG), is a glycoprotein-proteoglycan complex consisting of an N-linked glycoprotein of 250 kDa and a proteoglycan component >450 kDa. The core glycoprotein is present on the surface of melanoma cells, either as a free glycoprotein or modified by the addition of chondroitin sulfate. The structural features of MCSP include three (3) extracellular domains containing a total of ten (10) cysteines (five (5) potential disulfide bridges), fifteen (15) possible N-linked glycosylation sites, and eleven (11) potential chondroitin sulfate attachment sites. The transmembrane segment has a single cysteine, however, the functional significance of that residue has not been established. The cytoplasmic domain has three (3) threonine residues that may serve as sites for phosphorylation by protein kinase C, although it has not yet been shown that MCSP is phosphorylated.

MCSP is uniformly and abundantly expressed in most human melanoma lesions (Ferrone et al. (1988) Radiolabeled Monoclonal Antibodies for Imaging and Therapy Vol. 152, S. C. Srivastava, editor. Plenum Publishing Corp., New York/London. P. 55-73). MCSP has also been implicated in tumor invasion (Iida et al. (2001) J. Biol. Chem. 276:18786-18794). MCSP expression is an ominous prognostic factor in acral letiginous melanoma (Kageshita et al. (1993) Cancer Res. 53:2830-2833) and in nonmelanoma tumors such as infantile acute myeloid leukemia (Hilden et al. (1977) Blood 89:3801-3805).

The need exists for improved therapeutic antibodies against MCSP that are effective at treating and/or preventing tumors comprising cells expressing MCSP.

SUMMARY OF THE INVENTION

The present invention provides isolated antibodies (e.g., humanized or human antibodies) that bind to the membrane-proximal domain (MP) of human Melanoma-Associated Chondroitin Sulphate Proteoglycan (MCSP), and are capable of mediating cytolysis of a cell expressing MCSP in the presence of human effector cells or complement. Methods of using such antibodies to induce cytolysis (e.g., ADCC or CDCC) of cells expressing MP-MCSP are also provided.

By way of the present invention, it was discovered that the MP-MCSP is a particularly useful epitope on MCSP for inducing ADCC and/or CDCC against cells expressing MCSP, e.g., melanoma cells. Cytolysis of MCSP-expressing cells can be achieved using antibodies against MP-MCSP alone, or in the presence of an effector cell or complement. Cytotoxins or bispecific molecules that include such antibodies can also be used to induce cytolysis of cells which express MCSP.

Based on their ability to bind to cells expressing MCSP and mediate cytolysis of such cells, the antibodies, immunoconjugates, bispecific molecules and compositions of the present invention can be used in the treatment of a wide variety of diseases, e.g.; cancers involving cells which express MCSP. Such diseases include, but are not limited to, melanomas, glioblastomas, and breast cancer.

In one embodiment, the present invention provides a method of inducing cytolysis of a cell expressing MCSP by contacting the cell with an isolated antibody (e.g., a humanized or human antibody) that binds to the membrane-proximal domain of human MCSP in the presence of an effector cell or complement. Methods of inducing cytolysis of a cell expressing MCSP also include contacting the cell, in the presence of an effector cell or complement, with an isolated antibody generated by immunizing a subject with the membrane-proximal domain of human MCSP. Isolated antibodies that compete for binding with an antibody generated by immunizing a subject with the membrane-proximal domain of human MCSP can also be used to induce cytolysis of MCSP-expressing cells.

Methods of treating a disease involving cells expressing MCSP (e.g., melanoma cells) are also included in the present invention. Such methods include administering to a subject, suffering from the disease, an isolated antibody (e.g., a humanized or human antibody) that binds to the membrane-proximal domain of human MCSP, such that cytolysis of the cell occurs.

In another embodiment, a method for generating an immune response is provided by administering to a subject the membrane-proximal domain of MCSP, or an immunogenic portion thereof.

Cytolysis of the cell expressing MCSP can be mediated by a variety of mechanisms, e.g., ADCC or CDCC. In one embodiment, the antibody mediates cytolysis of at least 20% of the cells expressing MCSP.

Preferably, the antibody of the invention is a monoclonal antibody, such as a murine, humanized, chimeric, or fully human monoclonal antibody. In one aspect, the antibody binds to the membrane-proximal domain of human MCSP (e.g., the membrane-proximal domain of human MCSP having SEQ ID NO:2) with a $K_D$ of $10\times10^{-8}$ M or less, more preferably $1\times10^{-8}$ M or less, more preferably $5\times10^{-9}$ or less or even more preferably, $1\times10^{-9}$ or less.

The antibodies can be derivatized, linked to or co-expressed with another functional molecule. For example, an antibody of the invention can be functionally linked (e.g., by chemical coupling, genetic fusion, noncovalent association or otherwise) to one or more other molecular entities, such as another antibody (e.g., to produce a bispecific or a multispecific antibody), a cytoxin, a cellular ligand or an antigen. Bispecific and multispecific antibodies of the present invention which include a binding specificity for an Fc receptor (e.g., human FcγRI or human Fcα receptor) are useful for targeting a cell, e.g., an effector cell, to a tumor cell expressing MCSP, thereby resulting in cytolysis or phagocytosis of the tumor cell. Compositions comprising an antibody, immunoconjugate or bispecific molecule of the invention and a pharmaceutically acceptable carrier are also provided.

Methods of generating antibodies which bind to the membrane-proximal domain of MCSP and are capable of mediating cytolysis of a cell expressing MCSP in the presence of a human effector cell or complement are also provided in the present invention. Such methods include the steps of immunizing a subject with the membrane-proximal domain of human MCSP (e.g., the membrane-proximal domain of human MCSP having SEQ ID NO:2) and isolating the antibodies.

In another embodiment, the present invention provides a method for detecting in vitro or in vivo the presence of MP-MCSP in a sample, e.g., for diagnosing an MCSP-related disease. MCSP-expressing cells can be detected, for example, by contacting a sample to be tested, optionally along with a control sample, with a monoclonal antibody of the invention under conditions that allow for formation of a complex between the antibody and MP-MCSP. Complex formation is then detected (e.g., using an ELISA). When using a control sample along with the test sample, complex is detected in both samples and any statistically significant difference in the formation of complexes between the samples is indicative the presence of MCSP in the test sample.

Other features and advantages of the instant invention will be apparent from the following detailed description and examples which should not be construed as limiting. The contents of all references, Genbank entries, patents and published patent applications cited throughout this application are expressly incorporated herein by reference.

BRIEF DESCRIPTION OF THE DRAWINGS

FIG. 1 shows the amino acid sequence (SEQ ID NO: 1) of human MCSP. The membrane-proximal domain of MCSP (residues 1740-2221) is underlined (SEQ ID NO:2). The transmembrane domain is double underlined (residues 222-2246).

DETAILED DESCRIPTION OF THE INVENTION

Figure 2:
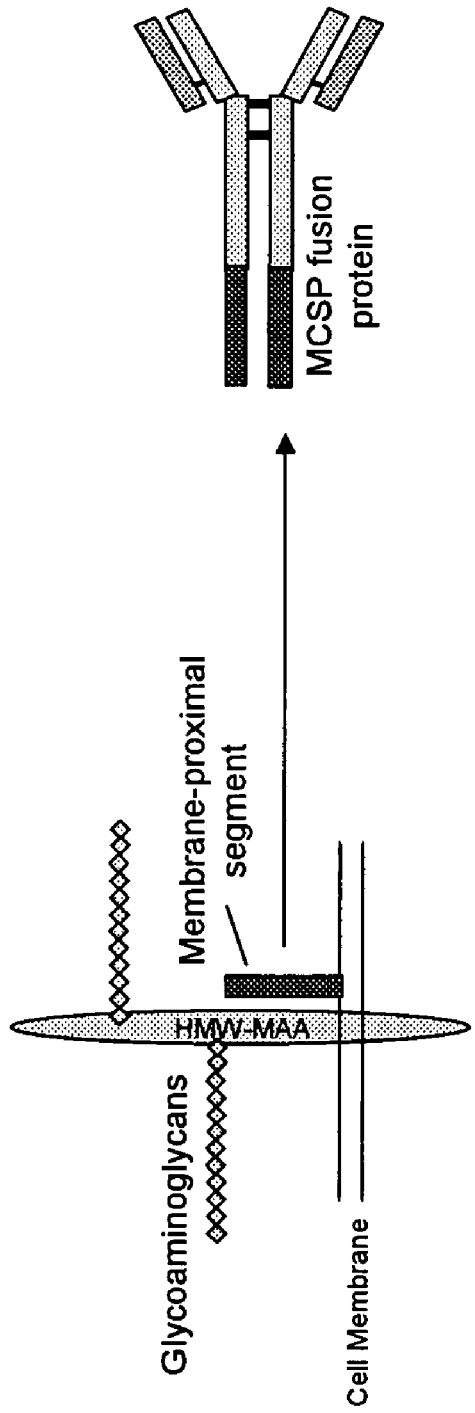
FIG. 2 schematically shows the MCSP antibody fusion protein comprising a human IGg antibody fused (at its C terminus) to the membrane-proximal domain of human MCSP ("MP-MCSP-IgG").

The present invention provides isolated antibodies (e.g., human or humanized antibodies) which bind to the membrane-proximal domain (MP) of human Melanoma-Associated Chondroitin Sulfate Proteoglycan (MCSP) and are capable of mediating cytolysis of a cell expressing MCSP in the presence of a human effector cell or complement. Other aspects of the invention include bispecific molecules, immunoconjugates and compositions which include such antibodies. Methods of generating the antibodies are also provided. Methods of using these molecules to treat diseases involving cells which express MCSP (e.g., melanomas) are further provided, including methods of inducing cytolysis of cells expressing MCSP, by administering the present antibodies either alone, or in the presence of an effector cell or complement. Antibodies can also be administered in the form of an immunoconjugate, a bispecific molecule, or a composition. Methods of generating an immune response against MCSP-expressing cells by administering to a subject the membrane-proximal domain of human MCSP (SEQ ID NO:2) or an immunogenic portion thereof, are also provided.

In order that the present invention may be more readily understood, certain terms are first defined. Additional definitions are set forth throughout the detailed description.

The terms "human Melanoma-Associated Chondroitin Sulfate Proteoglycan" (MCSP), "high molecular weight melanoma associated antigen" (HMW-MAA), "human melanoma proteoglycan" (HMP), "melanoma-associated proteoglycan antigen" (MPG) and "melanoma chondroitin sulfate proteoglycan" (mel-CSPG)) are used interchangeably and refer to the human glycoprotein-proteoglycan complex uniformly and abundantly expressed in most human melanoma lesions and consisting of an N-linked glycoprotein of 250 kDa and a proteoglycan component >450 kDa. The core glycoprotein is present on the surface of melanoma cells, either as a free glycoprotein or modified by the addition of chondroitin sulfate. The structural features of MCSP include three (3) extracellular domains containing a total of ten (10) cysteines (five (5) potential disulfide bridges), fifteen (15) possible N-linked glycosylation sites, and eleven (11) potential chondroitin sulfate attachment sites. The transmembrane segment has a single cysteine, however, the functional significance of that residue has not been established. The cytoplasmic domain has three (3) threonine residues that may serve as sites for phosphorylation by protein kinase C, although it has not yet been shown that MCSP is phosphorylated. The complete amino acid sequence of human MCSP protein has the amino acid sequence shown in SEQ ID NO:1 (Swiss-Prot Entry No. Q6UVK1) with the membrane-proximal domain (MP) comprising residues 1740-2221 (SEQ ID NO:2), as shown in FIG. 1.

As used herein, the term "cytolysis" refers to the destruction or killing of a cell. An antibody that is "capable of mediating cytolysis of a cell" is intended to refer to an antibody that is capable of killing of a cell (e.g., an MCSP-expressing cell). Cell cytolysis can occur by the antibody alone. Alternatively, cell cytolysis can occur, for example, using the antibody in the presence of a human effector cell or complement. The bispecific molecules, immunoconjugates and compositions described herein which include anti-MP-MCSP antibodies are also capable of mediating cytolysis of a cell expressing MCSP. Mechanisms by which cell cytolysis is achieved include, for example, effector cell functions, such as phagocytosis, antibody-dependent cell-mediated cytotoxicity (ADCC) or complement-dependent cell cytotoxicity (CDCC), cytokine release, and generation of superoxide anion.

As used herein, the term "effector cell" refers to an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Some effector cells express specific Fc receptors and carry out specific immune functions. In another embodiment, an effector cell is capable of inducing antibody-dependent cell-mediated cytotoxicity (ADCC), e.g., a neutrophil capable of inducing ADCC. For example, monocytes, macrophages, which express FcR are involved in specific killing of target cells and presenting antigens to other components of the immune system, or binding to cells that present antigens. In other embodiments, an effector cell can phagocytose a target antigen, target cell, or microorganism. The expression of a particular FcR on an effector cell can be regulated by humoral factors such as cytokines. For example, expression of FcγRI has been found to be up-regulated by G-CSF or GM-CSF. This enhanced expression increases the effector function of FcγRI-bearing cells against targets. An effector cell can phagocytose or lyse a target antigen or a target cell.

The term "antibody-dependent cellular cytotoxicity" or "ADCC" refers to a cell-mediated cytotoxic reaction in which an MCSP-expressing target cell with bound anti-MP-MCSP antibody is recognized by an effector cell bearing Fc receptors and is subsequently lysed without requiring the involvement of complement. The antibodies, by coating target cells, makes them vulnerable to attack by immune cells (e.g., natural killer cells or macrophages which have bound to their Fc receptors IgG specific for a target cell).

The term "complement-dependent cellular cytotoxicity" or "CDCC" refers to an immune response in which cell killing is achieved by activating complement. The "complement system" is a biochemical cascade of the immune system that works to clear pathogens and other target cells from an organism. It is derived from many small plasma proteins that work together to form the primary end result of cytolysis by disrupting the target cell's plasma membrane.

As used herein, the term "cytotoxic T lymphocyte (CTL) response" refers to an immune response induced by cytotoxic T cells. CTL responses are mediated primarily by CD8$^+$ T cells.

"Target cell" refers to any cell or pathogen whose elimination would be beneficial in a subject (e.g., a human or animal) and that can be targeted by an antibody of the invention (e.g., an anti-MP-MCSP antibody). For example, the target cell can be a cell expressing or overexpressing human MCSP.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., the membrane-proximal domain of human MCSP). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et at (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds the membrane-proximal domain of MCSP is substantially free of antibodies that specifically bind antigens other than the membrane-proximal domain of MCSP). An isolated antibody that specifically binds the membrane-proximal domain of human MCSP may, however, have cross-reactivity to other antigens, such as the membrane-proximal domain of MCSP molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "chimeric antibody", as used herein, refers to an antibody derived from a human antibody, but having a binding portion, i.e., the complementarity determining regions (CDRs), derived from a non-human antibody (e.g., a murine antibody), the CDRs being selected to provide the binding specificity of the chimeric antibody. Accordingly, the chimeric antibody has CDRs derived from a non-human antibody and the remaining portions of the antibody molecule are human.

The term "humanized antibody", as used herein, also refers to an antibody having portions derived from a human and a non-human antibody, but includes only the minimum amount of binding portion derived from a non-human antibody to confer binding specificity.

As used herein, "isotype" refers to the antibody class (e.g., IgM or IgG1) that is encoded by the heavy chain constant region genes.

The term "$K_{assoc}$" or "$K_a$", as used herein, is intended to refer to the association rate of a particular antibody-antigen interaction, whereas the term "$K_{dis}$" or "$K_d$", as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

As used herein, the term "subject" includes any human or nonhuman animal. The term "nonhuman animal" includes all vertebrates, e.g., mammals and non-mammals, such as non-human primates, sheep, dogs, cats, horses, cows chickens, amphibians, reptiles, etc.

Various aspects of the invention are described in further detail in the following subsections.

Anti-MP-MCSP Antibodies

Antibodies of the present invention are characterized by binding to MP-MCSP (e.g., SEQ ID NO:2) and mediating cytotoxicity of cells expressing MCSP (e.g., mediating antibody dependent cell-mediated cytotoxicity (ADCC), complement-dependent cell-mediated cytotoxicity (CDCC), cytokine release, phagocytosis, and/or generation of superoxide anion).

Standard assays to evaluate the ability of the antibodies to bind human MCSP are known in the art, including for example, Enzyme-Linked ImmunoSorbent Assays (ELISAs), Western blots and RadioImmunAssays (RIAs). Suitable assays are described in detail in the Examples. The binding kinetics (e.g., binding affinity) of the antibodies also can be assessed by standard assays known in the art, such as by Biacore analysis.

Similarly, standard assays to evaluate the cytolytic effects of the antibodies on cells expressing human MCSP are known in the art and described in further detail in the Examples.

Preferred antibodies mediate cytolysis of at least 10%, 15%, 20%, 25%, 30% or more of cells expressing MCSP. Values and ranges included and/or intermediate within the ranges set forth herein are also intended to be within the scope of the present invention.

Antibodies Generated by Immunization with MP-MCSP

In another embodiment, the invention provides methods for generating antibodies which bind to human MP-MCSP by administering MP-MCSP, or an immunogenic fragment thereof, to a subject and isolating anti-MP-MCSP antibodies.

Antibodies that bind to the same domain of MCSP as do the antibodies exemplified herein are also provided. Such antibodies can be identified based on their ability to cross-compete (e.g., to competitively inhibit the binding of, in a statistically significant manner) with the anti-MP-MCSP antibodies specifically described in the Examples, in standard binding assays. The ability of a test antibody to inhibit the binding of antibodies to human MCSP demonstrates that the test antibody can compete with that antibody for binding to human MCSP. Such an antibody may, according to non-limiting theory, bind to the same or a related (e.g., a structurally similar or spatially proximal) epitope on human MCSP as the antibody with which it competes. In a preferred embodiment, the antibody that binds to the same epitope on human MCSP as the anti-MP-MCSP antibody exemplified herein is a human or humanized monoclonal antibody. Such human monoclonal antibodies can be prepared and isolated as described in the following: U.S. Pat. Nos. 5,545,806; 5,569, 825; 5,625,126; 5,633,425; 5,789,650; 5,877,397; 5,661,016; 5,814,318; 5,874,299; and 5,770,429; all to Lonberg and Kay.

Production of Monoclonal Antibodies of the Invention

Monoclonal antibodies (mAbs) of the present invention can be produced by a variety of techniques, including conventional monoclonal antibody methodology e.g., the standard somatic cell hybridization technique of Kohler and Milstein (1975) *Nature* 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In a preferred embodiment, the antibodies of the invention are human monoclonal antibodies. Such human monoclonal antibodies directed against human MCSP can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode unrearranged human heavy (μ and κ) and κ light chain immunoglobulin sequences, together with targeted mutations that inactivate the endogenous μ and κ chain loci (see e.g., Lonberg, et al. (1994) Nature 368(6474): 856-859). Accordingly, the mice exhibit reduced expression of mouse IgM or □, and in response to immunization, the introduced human heavy and light chain transgenes undergo class switching and somatic mutation to generate high affinity human IgGκ monoclonal (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol.* 13: 65-93, and Harding, F. and Lonberg, N. (1995) *Ann. N.Y. Acad. Sci.* 764:536-546). The preparation and use of HuMab mice, and the genomic modifications carried by such mice, is further described in Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Taylor, L. et al. (1994) *International Immunology* 6: 579-591; and Fishwild, D. et al. (1996) *Nature Biotechnology* 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes, such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise anti-MCSP antibodies of the invention. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-MCSP antibodies of the invention. For example, mice carrying both a human heavy chain transchromosome and a human light chain transchromosome, referred to as "TC mice" can be used; such mice are described in Tomizuka et al. (2000) *Proc. Natl. Acad. Sci. USA* 97:722-727. Furthermore, cows carrying human heavy and light chain transchromosomes have been described in the art (Kuroiwa et al. (2002) *Nature Biotechnology* 20:889-894) and can be used to raise anti-MCSP antibodies of the invention.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Generation of Transfectomas Producing Monoclonal Antibodies of the Invention

Antibodies of the invention also can be produced in a host cell transfectoma using, for example, a combination of recombinant DNA techniques and gene transfection methods as is well known in the art (e.g., Morrison, S. (1985) *Science* 229:1202).

For example, to express the antibodies, or antibody fragments thereof, DNAs encoding partial, or full-length, light and heavy chains can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SR☐ promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. In particular, for use with NS0 myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Characterization of Antibody Binding to Antigen

Antibodies of the invention can be tested for binding to MCSP by, for example, standard ELISA. Briefly, microtiter plates are coated with purified MCSP at 0.25 μg/ml in PBS, and then blocked with 5% bovine serum albumin in PBS. Dilutions of antibody (e.g., dilutions of plasma from MCSP-immunized mice) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to alkaline phosphatase for 1 hour at 37° C. After washing, the plates are developed with pNPP substrate (1 mg/ml), and analyzed at OD of 405-650. Preferably, mice which develop the highest titers will be used for fusions.

An ELISA assay as described above can also be used to screen for hybridomas that show positive reactivity with MCSP immunogen. Hybridomas that bind with high avidity to MCSP are subcloned and further characterized. One clone from each hybridoma, which retains the reactivity of the parent cells (by ELISA), can be chosen for making a 5-10 vial cell bank stored at −140° C., and for antibody purification.

To purify anti-MCSP antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

To determine if the selected anti-MCSP monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using MCSP coated-ELISA plates as described above. Biotinylated mAb binding can be detected with a strep-avidin-alkaline phosphatase probe.

To determine the isotype of purified antibodies, isotype ELISAs can be performed using reagents specific for antibodies of a particular isotype. For example, to determine the isotype of a human monoclonal antibody, wells of microtiter plates can be coated with 1 μg/ml of anti-human immunoglobulin overnight at 4° C. After blocking with 1% BSA, the plates are reacted with 1 μg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

Anti-MCSP human IgGs can be further tested for reactivity with MCSP antigen by Western blotting. Briefly, MCSP can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Immunoconjugates

In another aspect, the present invention features an anti-MP-MCSP antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg™; Wyeth-Ayerst).

Cytoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) Adv. Drug Deliv. Rev. 55:199-215; Trail, P. A. et al. (2003) Cancer Immunol. Immunother. 52:328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3:1089-1091; Senter, P. D. and Springer, C. J. (2001) Adv. Drug Deliv. Rev. 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine[131], indium[111], yttrium[90] and lutetium[177]. Method for preparing radioimmunconjugates are established in the art. Examples of radioimmunoconjugates are commercially available, including Zevalin™ (IDEC Pharmaceuticals) and Bexxar™ (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et at (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al, "The Preparation And Cytotoxic Properties Of Antibody-Toxin Conjugates", Immunol. Rev., 62:119-58 (1982).

Bispecific Molecules

In another aspect, the present invention features bispecific molecules comprising an anti-MCSP antibody, or a fragment thereof, of the invention. An antibody of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for MCSP and a second binding specificity for a second target epitope. In a particular embodiment of the invention, the second target epitope is an Fc receptor, e.g., human FcγRI (CD64) or a human Fcα receptor (CD89). Therefore, the invention includes bispecific molecules capable of binding both to FcγR, FcαR or FcεR expressing effector cells (e.g., monocytes, macrophages or polymorphonuclear cells (PMNs)), and to target cells expressing MCSP. These bispecific molecules target MCSP expressing cells to effector cell and trigger Fc receptor-mediated effector cell activities, such as phagocytosis of an MCSP expressing cells, antibody dependent cell-mediated cytotoxicity (ADCC), cytokine release, or generation of superoxide anion.

In one embodiment, the bispecific molecules of the invention comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγreceptor classes: FcγRI (CD64), FcγRII (CD32), and FcγRIII (CD16). In one preferred embodiment, the Fcγ receptor a human high affinity FcγRI. The human FcγRI is a 72 kDa molecule, which shows high affinity for monomeric IgG ($10^8$-$10^9$ M$^{-1}$).

The production and characterization of certain preferred anti-Fcγmonoclonal antibodies are described by Fanger et al. in PCT Publication WO 88/00052 and in U.S. Pat. No. 4,954,617, the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the H22 antibody is described in Graziano, R. F. et al. (1995) *J. Immunol* 155 (10): 4996-5002 and PCT Publication WO 94/10332. The H22 antibody producing cell line was deposited at the American Type Culture Collection under the designation HA022CL1 and has the accession no. CRL 11177.

In still other preferred embodiments, the binding specificity for an Fc receptor is provided by an antibody that binds to a human IgA receptor, e.g., an Fc-alpha receptor (FcαRI (CD89)), the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity ($\approx 5 \times 10^7$ M$^{-1}$) for both IgA1 and IgA2, which is increased upon exposure to cytokines such as G-CSF or GM-CSF (Morton, H. C. et al. (1996) *Critical Reviews in Immunology* 16:423-440). Four FcαRI-specific monoclonal antibodies, identified as A3, A59, A62 and A77, which bind FcαRI outside the IgA ligand binding domain, have been described (Monteiro, R. C. et al. (1992) *J. Immunol.* 148: 1764).

FcαRI and FcγRI are preferred trigger receptors for use in the bispecific molecules of the invention because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); (4) mediate enhanced antigen presentation of antigens, including self-antigens, targeted to them.

While human monoclonal antibodies are preferred, other antibodies which can be employed in the bispecific molecules of the invention are murine, chimeric and humanized monoclonal antibodies.

The bispecific molecules of the present invention can be prepared by conjugating the constituent binding specificities, e.g., the anti-FcR and anti-MCSP binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio) propionate (SPDP), and sulfosuccinimidyl 4-(N-maleimidomethyl)cyclohaxane-1-carboxylate (sulfo-SMCC) (see e.g., Karpovsky et al. (1984) *J. Exp. Med.* 160: 1686; Liu, M A et al. (1985) *Proc. Natl. Acad. Sci. USA* 82:8648). Other methods include those described in Paulus (1985) Behring Ins. Mitt. No. 78, 118-132; Brennan et al. (1985) *Science* 229:81-83), and Glennie et al. (1987) *J. Immunol.* 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand× Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γcounter or a scintillation counter or by autoradiography.

Pharmaceutical Compositions

In another aspect, the present invention provides a composition, e.g., a pharmaceutical composition, containing one or a combination of monoclonal antibodies, or antigen-binding portion(s) thereof, of the present invention, formulated together with a pharmaceutically acceptable carrier. Such compositions may include one or a combination of (e.g., two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

Pharmaceutical compositions of the invention also can be administered in combination therapy, i.e., combined with other agents. For example, the combination therapy can include an anti-MCSP antibody of the present invention combined with at least one other anti-inflammatory or immunosuppressant agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjuage, or bispecific molecule, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-MCSP antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-MCSP antibody of the invention preferably results in a decrease in severity of disease symptoms, an increase in frequency and duration of disease symptom-free periods, or a prevention of impairment or disability due to the disease affliction. In the case of Rheumatoid Arthritis (RA), a therapeutically effective dose preferably prevents further deterioration of physical symptoms associated with RA, such as, for example, pain, fatigue, morning stiffness (lasting more than one hour), diffuse muscular aches, loss of appetite, weakness, joint pain with warmth, swelling, tenderness, and stiffness of a joint after inactivity. A therapeutically effective dose preferably also prevents or delays onset of RA, such as may be desired when early or preliminary signs of the disease are present. Likewise it includes delaying chronic progression associated with RA. Laboratory tests utilized in the diagnosis of RA include chemistries (including the measurement of MCSP levels), hematology, serology and radiology. Accordingly, any clinical or biochemical assay that monitors any of the foregoing may be used to determine whether a particular treatment is a therapeutically effective dose for treating RA. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p 120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

Uses and Methods of the Invention

Based on their ability to bind to cells expressing MCSP and mediate cytolysis of such cells, the antibodies, immunoconjugates, bispecific molecules and compositions of the present invention can be used in the treatment of a wide variety of diseases, e.g., cancers involving cells which express MCSP. Such diseases include, but are not limited to, melanomas, glioblastomas and breast cancer.

For use in therapy, cytolysis of a cell expressing human MCSP is achieved by contacting the cell with an antibody (immunoconjugate or bispecific molecule) of the present invention which binds to the membrane-proximal domain of human MCSP in the presence of an effector cell or complement. Antibodies generated by immunizing a subject with the membrane-proximal domain of human MCSP can also be used, as well as antibodies that compete for binding with an antibody generated by immunizing a subject with the membrane-proximal domain of human MCSP.

In another embodiment, the membrane-proximal domain of human MCSP, or an antigenic portion thereof, can be used to generate an immune response in a subject. For example, the MP-MCSP (e.g., the MP-MCSP comprising SEQ ID NO:2) is administered to a subject in sufficient quantities to generate anti-MP-MCSP antibodies. As used herein, an "antigenic portion" refers to a portion of the MP-MCSP that is capable of stimulating the production of an antibody when introduced into a subject.

The term "subject" as used herein in intended to include human and non-human animals. Non-human animals include all vertebrates, e.g., mammals and non-mammals, such as non-human primates, sheep, dogs, cats, cows, horses, chickens, amphibians, and reptiles. The methods are particularly suitable for treating human patients having a disorder associated with aberrant MCSP expression. When antibodies to MCSP are administered together with another agent, the two can be administered in either order or simultaneously.

Diagnostic methods are also provided. For example, the anti-MP-MCSP antibodies can be used in vitro or in vivo to diagnose diseases mediated by MP-MCSP. The antibodies of the invention can be used to detect levels of MP-MCSP, or levels of cells which contain MP-MCSP on their membrane surface, which levels can then be linked to certain disease symptoms. Standard assays for detecting and measuring such levels are well known in the art and can be achieved by contacting a sample and a control sample with the anti-MP-MCSP antibody under conditions that allow for the formation of a complex between the antibody and MP-MCSP. Any complexes formed between the antibody and MP-MCSP are detected and compared in the sample and the control.

In all cases, the antibodies are administered in an effective amount to exert their desired therapeutic effect. The term "effective amount" refers to that amount necessary or sufficient to realize a desired biologic effect. For example, an effective amount could be that amount necessary to eliminate a specific amount of tumor cells expressing MCSP. The effective amount for any particular application can vary depending on such factors as the disease or condition being treated, the particular conjugate being administered, the size of the subject, or the severity of the disease or condition. One of ordinary skill in the art can empirically determine the effective amount of a particular multispecific molecule without necessitating undue experimentation.

Preferred routes of administration include, for example, injection (e.g., subcutaneous, intravenous, parenteral, intraperitoneal, intrathecal). The injection can be in a bolus or a continuous infusion. Other routes of administration include oral administration.

The antibodies of the invention also can be coadministered with adjuvants and other therapeutic agents, such as immunostimulatory agents. The conjugates are typically formulated in a pharmaceutically acceptable carrier alone or in combination with such agents. Examples of such carriers include solutions, solvents, dispersion media, delay agents, emulsions and the like. The use of such media for pharmaceutically active substances is well known in the art. Any other conventional carrier suitable for use with the molecules falls within the scope of the instant invention.

Suitable agents for co-administration include other antibodies, cytotoxins and/or drugs. In one embodiment, the agent is an anti-CTLA-4 antibody which is known to aid or induce immune responses. In another embodiment, the agent is a chemotherapeutic agent. The antibodies also can be administered in combination with radiation.

Also within the scope of the invention are kits comprising the compositions (e.g., antibodies, human antibodies, immunoconjugates and bispecific molecules) of the invention and instructions for use. The kit can further contain a least one additional reagent, or one or more additional antibodies of the invention (e.g., an antibody having a complementary activity which binds to an epitope on the target antigen distinct from the first antibody). Kits typically include a label indicating the intended use of the contents of the kit. The term label includes any writing, or recorded material supplied on or with the kit, or which otherwise accompanies the kit.

The present invention is further illustrated by the following examples which should not be construed as further limiting. The contents of all figures and all references, patents and published patent applications cited throughout this application are expressly incorporated herein by reference.

EXAMPLES

Example 1

Production of MP-MCSP-IgG i) MCSP Conjugate:

A fusion protein comprising a human IGg antibody fused (at its C terminus) to the membrane-proximal domain of human MCSP ("MP-MCSP-IgG") was generated by linking the membrane-proximal (MP) domain of MCSP antigen (amino acids 1740 to 2221 of human MCSP; "MP-MSCP") to the human IgG antibody. Linkage was accomplished by covalently attaching the antigen to the heavy chain of the antibody by way of a genetic fusion, as shown schematically in FIG. 2.

ii) Recombinant Expression of MCSP Conjugate:

A plasmid containing neomycin and dihydrofolate reductase genes was generated containing the MP-MCSP-IgG coding sequence. The resulting plasmid construct was transfected into CHO cells using a standardized protocol (Invitrogen). Transfected cells were selected in media containing the antibiotic G418. To confirm expression, Western Blot analysis of proteins run on SDS-PAGE under reducing conditions was performed. This fusion protein was observed to be of the expected molecular weight and to be properly assembled. The resulting fusion protein was purified using a Protein A column under standard conditions.

Example 2

Preparation of Rabbit Anti-MP-MCSP IgG i) Rabbit Immunization

Three (3) New Zealand White rabbits were immunized with 200 μg of MP-MCSP conjugate from Example 1 in Complete Freund's Adjuvant. Rabbits were then further immunized with 200 μg of MP-MCSP conjugate in Incomplete Freunds Adjuvant on days 21 and 42 and an exsanguination bleed was performed on day 57. IgG1 antibodies were recovered from serum and purified on a Protein A column under standard conditions.

ii) Depletion of Anti-Human Antibodies

To deplete anti-human antibodies, a human IgG agarose column (Sigma) was equilibrated with 5-10 column volumes of BupH PBS binding buffer (Pierce) and the protein A eluate from (i) above was then loaded and eluted. The IgG agarose purification process was repeated with the eluate to yield the rabbit anti-MP-MCSP antibody preparation.

Example 3

Binding of Anti-MP-MCSP Antibodies to Melanoma Cells

Figure 3:
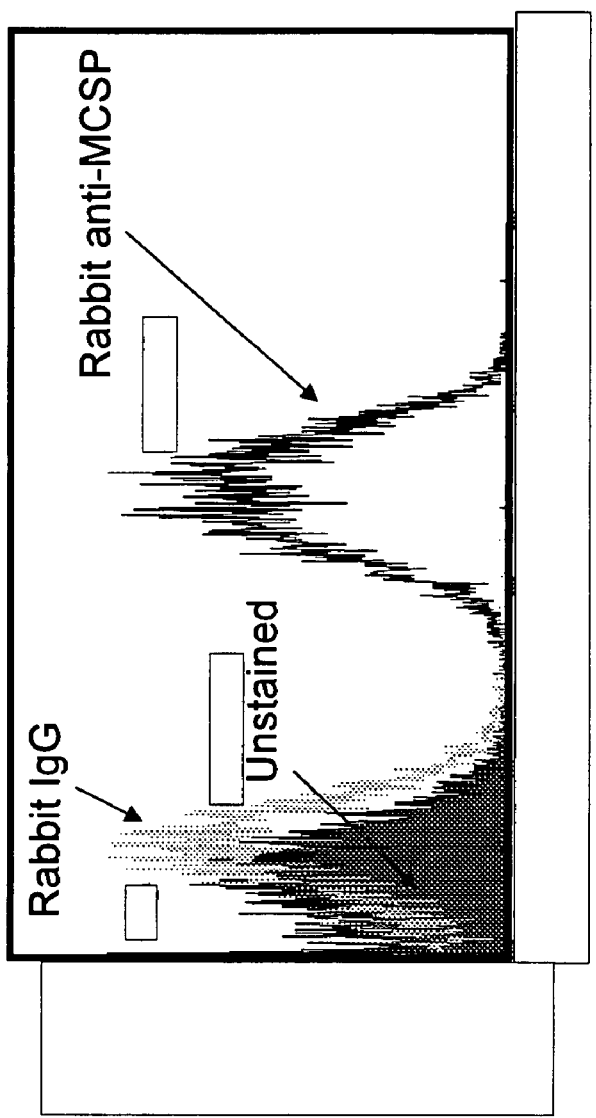
FIG. 3 is a graph showing the binding of anti-MP-MCSP antibody to melanoma cells.
Figure 4:
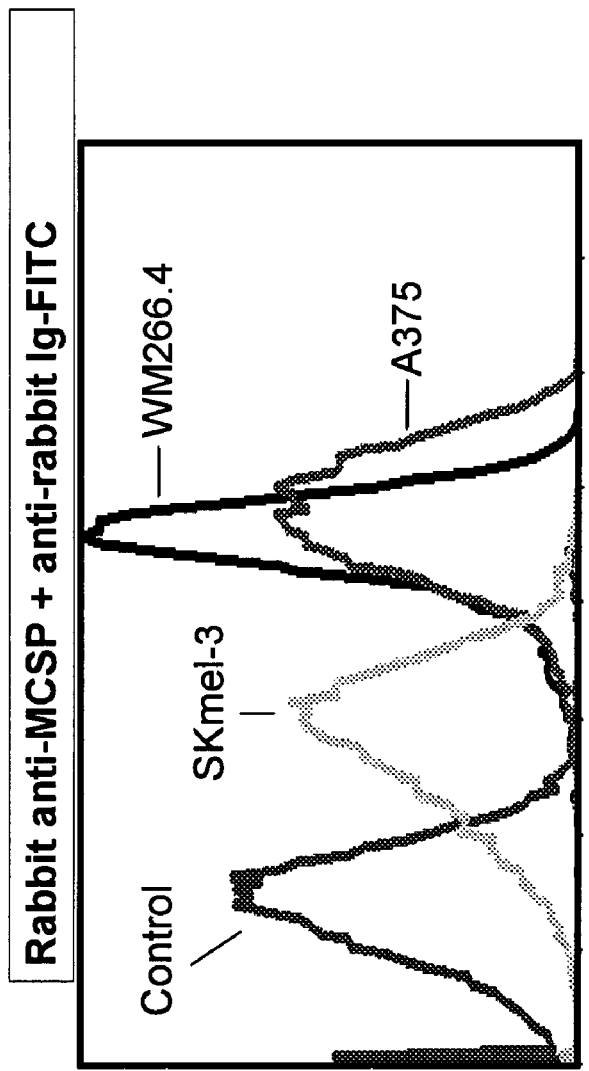
FIG. 4 is a graph showing that anti-MP-MCSP antibody detects MCSP expression on melanoma cells lines WM266.4, A375, and Skmel-3.

Target cells (melanoma cell lines) were incubated with the anti-MP-MCSP antibody preparation from Example 2 or an isotype control. Antibodies were detected with a FITC-labeled anti-rabbit Ig secondary antibody. The cell associated fluorescence was determined using a flow cytometer. Results are shown in FIGS. 3 and 4.

Example 4

Antibody Dependent Cell Cytotoxicity (ADCC)

Figure 5:
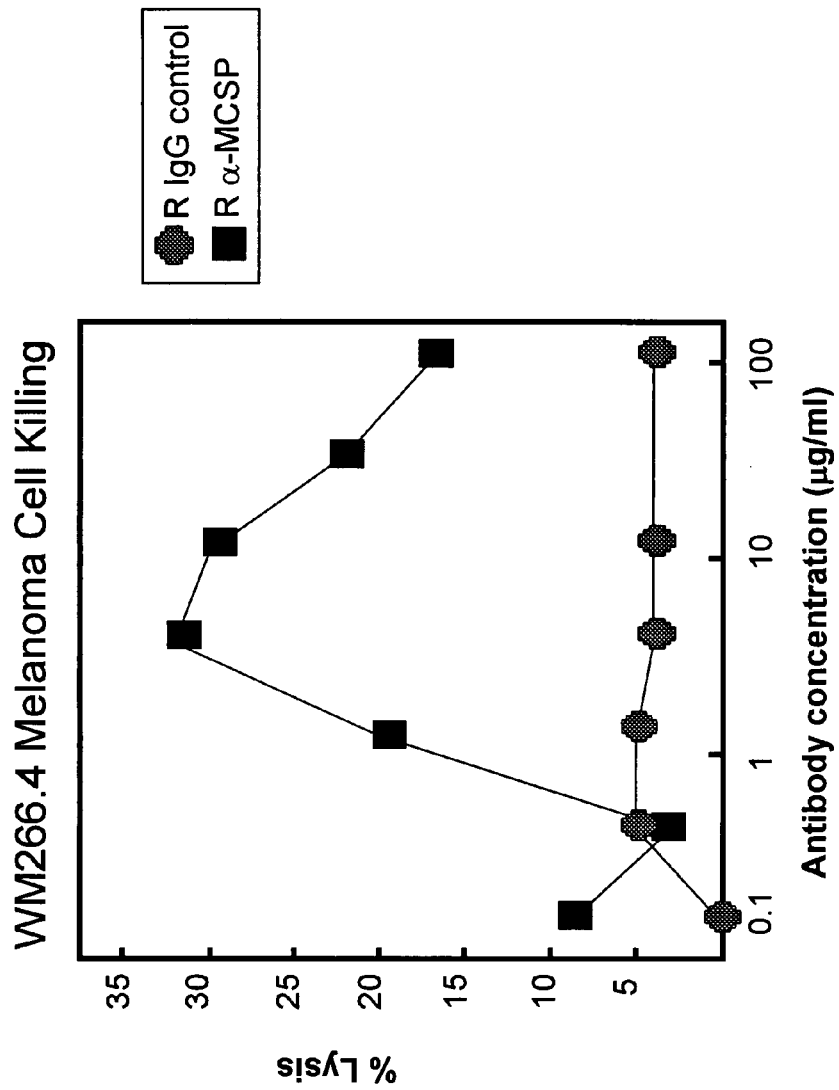
FIG. 5 is a graph showing the cytotoxic cell killing activity via ADCC of anti-MP-MCSP conjugates.

The concentration of the anti-MP-MCSP antibody preparation from Example 2 was adjusted in R10 buffer (RPMI+ 10% FBS). Antibody was added at a range of concentrations to wells in a V-bottom plate (Costar). Human peripheral blood mononuclear cells (PBMCs) and target cells (WM266.4 or A375 cell lines) were added to each well and lysis was measured using a Promega CytoTox 96® Non-Radioactive Cytotoxicity Assay Kit according to the manufacturer's directions. Results are shown in FIG. 5, from which it can be seen that the anti-MP-MCSP antibodies mediated significant ADCC compared to control.

Example 5

Complement Dependent Cell Cytotoxicity (CDCC)

Figure 6:
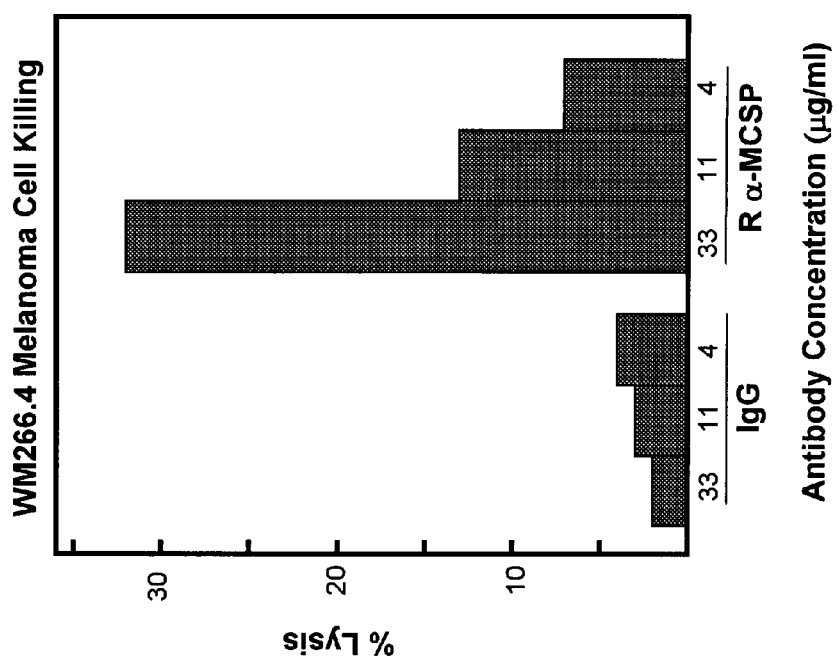
FIG. 6 is a graph showing the cytotoxic cell killing activity via CDCC of anti-MP-MCSP conjugates.

The antibody preparation from Example 2 was adjusted in R10 buffer (RPMI+10% FBS). The preparation was added to wells in a V-bottom plate (Costar). Target cells (WM266.4 or A375 cell lines) and a source of complement were added to each well and lysis was measured using a Promega CytoTox 96® Non-Radioactive Cytotoxicity Assay Kit according to the manufacturer's directions. Results are shown in FIG. 6, from which it can be seen that the anti-MP-MCSP antibodies mediated significant CDCC compared to control.

Example 6

Cytotoxicity Assay (Autologous DCs)

Figure 7:
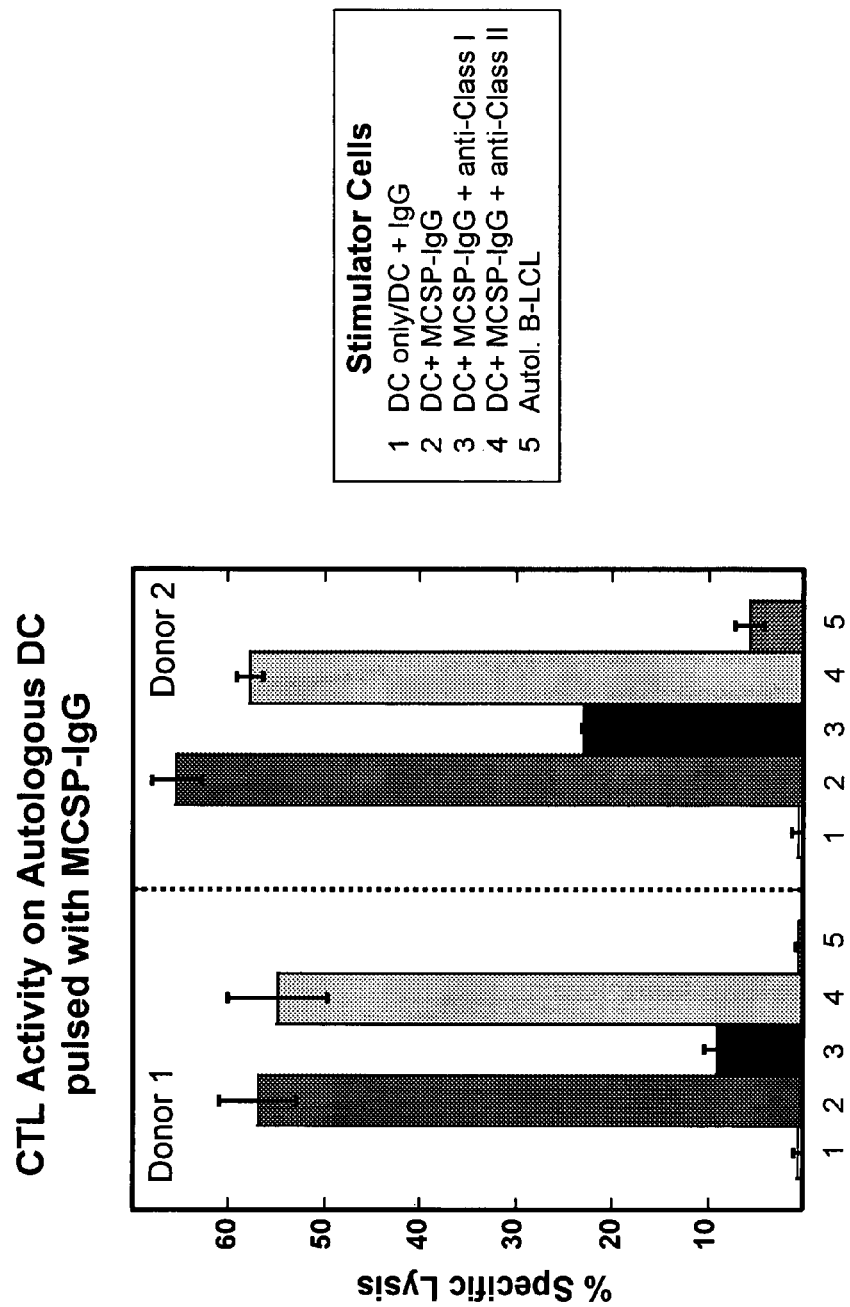
FIG. 7 is a graph showing the CTL activity on autologous dendritic cells, expressed as % Specific Lysis, of the MP-MCSP antibody fusion protein.

Autologous dendritic cells, either alone, with control antibody, or antigen loaded with MP-MCSP-IgG from Example 1, were washed twice in RPMI medium and the pellet was resuspended and labeled with $Na_2{}^{51}CrO_4$ for about an hour at 37° C. The labeled target cells were washed in RPMI medium and the pellet resuspended. Antigen-specific effector T-cells (expanded in vitro by stimulating bulk peripheral human lymphocytes for 3-4 rounds of stimulation with autologous dendritic cells pre-loaded with MP-MCSP-IgG) were titrated in a V-bottomed plate to give ratios of 100:1 (effector T cell, E: target, T) through to 12.5:1 or lower. A constant number of labeled targets were added and the plates were spun down at low speed and incubated at 37° C. After 4 hours supernatant was harvested and the radioactivity released was determined in a gamma-counter (Wallac Instruments, Perkin-Elmer). CTL activity was calculated and expressed as % Specific Lysis (killing) using the following equation:

Specific Lysis(%)=Experimental Release(cpm)−Spontaneous Release(cpm)Maximal Release(cpm)−Spontaneous Release(cpm)×100 where Experimental (cpm) refers to radioactivity (chromium released) from wells containing CTL (E) and target (T); Spontaneous (cpm) refers to the radioactivity from wells with targets in 0.1 ml medium alone (i.e., no CTL added) while Maximal release refers to radioactivity from wells with targets in the presence of 0.1 ml detergent solution. For MHC blocking analysis, labeled targets were preincubated with HLA-specific mAbs, at room temperature. Unbound mAb was removed by centrifugation and mAb-coated targets were added to CTL. Results are shown in FIG. 7.

Example 7

Cytotoxicity Assay (Melanoma Cell Lines)

Figure 8:
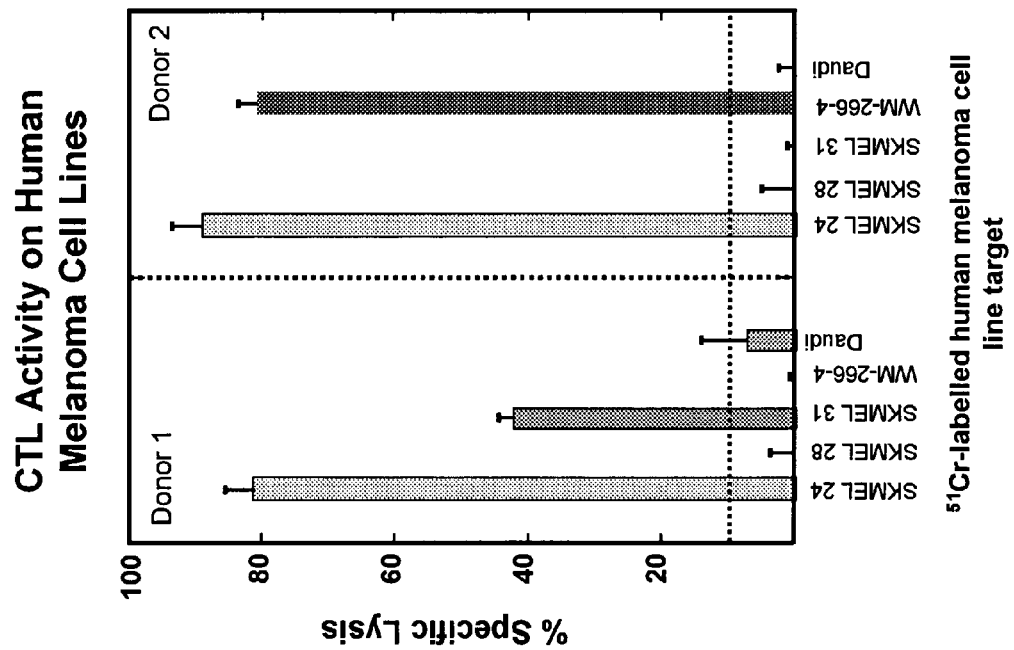
FIG. 8 is a graph showing the CTL activity on human melanoma cells, expressed as % Specific Lysis, of the MP-MCSP antibody fusion protein.

The procedure of Example 5 was repeated with a series of Melanoma cell lines as target cells. Results are shown in FIG. 8.

Example 8

Human T-Cell Proliferative Responses to MP-MCSP

Figure 9:
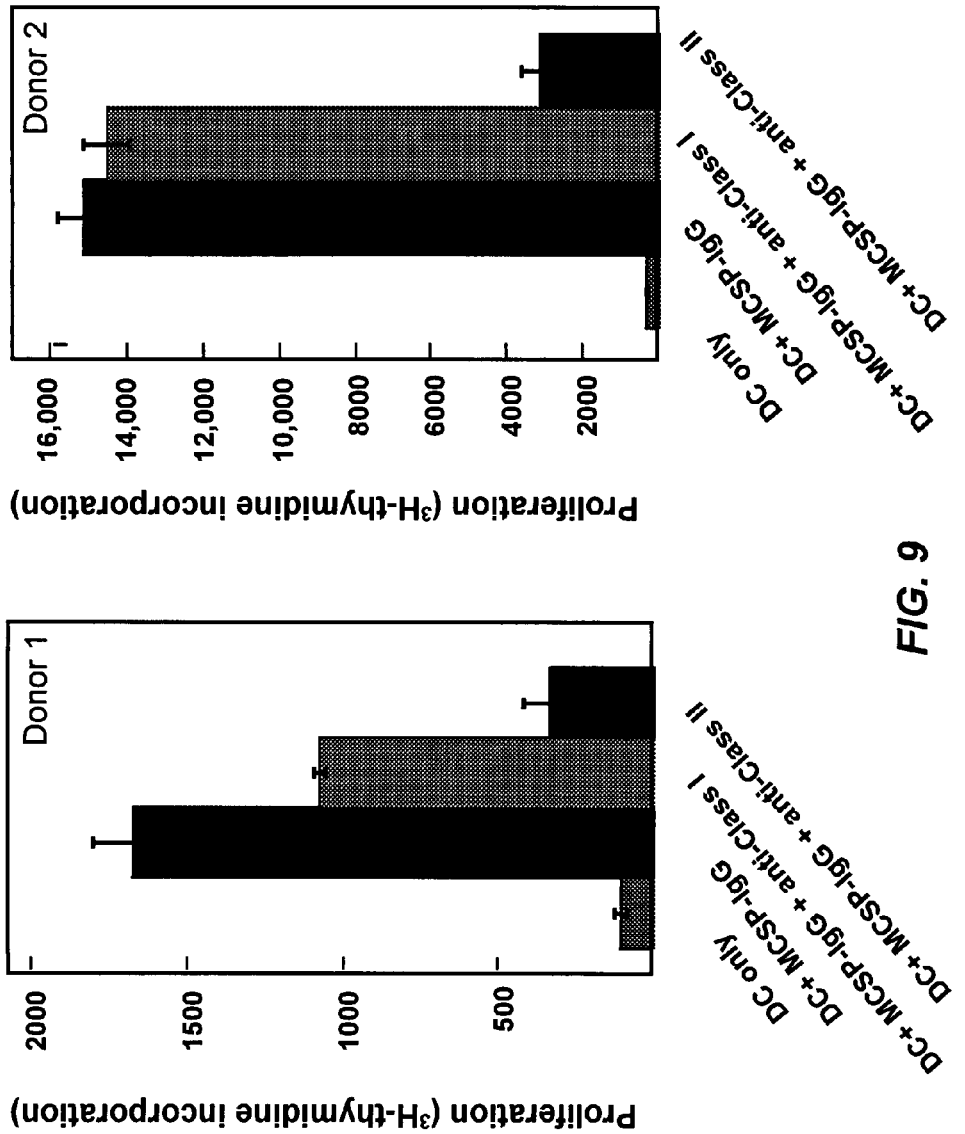
FIGS. 9A (donor 1) and 9B (donor 2) are graphs showing human T-cell proliferative responses to MCSP using the MP-MCSP antibody fusion protein.

Effector T cells raised as in Example 6 were co-cultured with autologous DCs loaded with or without MCSP antigen in flat bottomed microplates. The mixture was co-cultured at 37° C. On day 4, cultures were pulsed with $^3$H-thymidine and 18 hours later, cells were harvested directly on filters (Millipore). Filters were washed three times with water followed by one wash in ethanol and allowed to dry under the hood. Scintillation fluid (Packard, 20 µl/well) was then added to the filters. Filter-bound radioactivity was determined by counting on a Wallac beta counter. The results are expressed as mean cpm of $^3$H-thymidine incorporated. For MHC blocking analysis, labeled targets were preincubated with HLA-specific mAbs at room temperature. Unbound mAb was removed by centrifugation. Results are shown in FIG. 9.

EQUIVALENTS

Those skilled in the art will recognize, or be able to ascertain using no more than routine experimentation, many equivalents of the specific embodiments of the invention described herein. Such equivalents are intended to be encompassed by the following claims.

| SUMMARY OF SEQUENCE LISTING | |
|---|---|
| SEQ ID NO: | SEQUENCE |
| 1 | Amino acid sequence of human MCSP |
| 2 | Amino acid sequence of the membrane-proximal domain of human MCSP |

We claim:

1. A method of inducing cytolysis of a cell expressing human Melanoma-Associated Chondroitin Sulphate Proteoglycan (MCSP), comprising contacting the cell in the presence of an effector cell or complement with an antibody that binds to the membrane-proximal domain of human MCSP (SEQ ID NO:2), such that cytolysis of the cell occurs.

2. The method of claim 1, wherein the antibody is generated by immunizing a subject with the membrane-proximal domain of human MCSP.

3. The method of claim 1, wherein the antibody competes for binding with an antibody generated by immunizing a subject with the membrane-proximal domain of human MCSP.

4. The method of claim 1, wherein the antibody is administered to a subject suffering from a disease involving cells expressing MCSP.

5. The method of claim 1, wherein the antibody mediates cytolysis of the cells by a mechanism selected from the group consisting of phagocytosis, antibody dependent cell-mediated cytotoxicity (ADCC), complement-dependent cell-mediated cytotoxicity (CDCC), cytokine release, and generation of superoxide anion.

6. The method of claim 1, wherein the antibody is selected from the group consisting of a polyclonal antibody, a monoclonal antibody, a chimeric antibody, a humanized antibody and a human antibody.

7. The method of claim 1, wherein the antibody binds to MCSP with a dissociation constant ($K_D$) of $10 \times 10^{-8}$ M.

8. The method of claim 1, wherein the antibody mediates cytolysis of at least 20% of the cells expressing MCSP.

9. The method of claim 1, wherein the antibody is conjugated to a binding specificity for an Fc receptor.

10. The method of claim 1, wherein the antibody is conjugated to a cytotoxin.

11. The method of claim 1, wherein the cell is a melanoma cell.

12. An isolated antibody which binds to the membrane-proximal domain of human MCSP (SEQ ID NO:2) and wherein the antibody is capable of mediating cytolysis of a cell expressing MCSP in the presence of a human effector cell or complement.

13. The antibody of claim 12, wherein the antibody is generated by immunizing a subject with the membrane-proximal domain of human MCSP.

14. An isolated antibody that competes for binding with the antibody of claim 12 or 13.

15. The antibody of claim 12, wherein the antibody mediates cytolysis of cells by a mechanism selected from the group consisting of phagocytosis, antibody dependent cell-mediated cytotoxicity (ADCC), complement-dependent cell-mediated cytotoxicity (CDCC), cytokine release, and generation of superoxide anion.

16. The antibody of claim 12, wherein the antibody is selected from the group consisting of a polyclonal antibody, a monoclonal antibody, a chimeric antibody, a humanized antibody and a human antibody.

17. The antibody of claim 12, wherein the antibody binds to MCSP with a dissociation constant ($K_D$) of $10 \times 10^{-8}$ M.

18. The antibody of claim 12, wherein the antibody mediates cytolysis of at least 20% of the cells expressing MCSP.

19. The antibody of claim 12, further comprising a cytotoxic moiety.

20. A bispecific molecule comprising the antibody of claim 12 and a binding specificity for an Fc receptor.

21. The bispecific molecule of claim 20 wherein the Fc receptor is a human FcγRI or a human Fcα receptor.

22. The bispecific molecule of claim 20, which binds to the Fc receptor at a site which is distinct from the immunoglobulin binding site of the receptor.

23. A composition comprising the antibody of claim 12 or the bispecific molecule of claim 22 and a pharmaceutically acceptable carrier.

24. A method of generating the isolated antibody of claim 12 that binds to the membrane-proximal domain of human MCSP, comprising the steps of (a) immunizing a subject with the membrane-proximal domain of human MCSP (SEQ ID NO:2), and (b) isolating the antibody, wherein the antibody is capable of mediating cytolysis of a cell expressing MCSP in the presence of human effector cells.

25. A method of generating an immune response in a subject, comprising the steps of (a) vaccinating the subject with the membrane-proximal domain of human MCSP (SEQ ID NO:2), or immunogenic portion thereof, and (b) generating antibodies against the domain.

* * * * *

UNITED STATES PATENT AND TRADEMARK OFFICE
CERTIFICATE OF CORRECTION

PATENT NO. : 8,318,165 B2
APPLICATION NO. : 12/439912
DATED : November 27, 2012
INVENTOR(S) : Tibor Keler et al.

It is certified that error appears in the above-identified patent and that said Letters Patent is hereby corrected as shown below:

At column 40, claim number 23, line numbers 51-52, please change "the bispecific molecule of claim 22 and a pharmaceutically acceptable carrier." to --the bispecific molecule of claim 20 and a pharmaceutically acceptable carrier.--

Signed and Sealed this
Second Day of April, 2013

Teresa Stanek Rea
*Acting Director of the United States Patent and Trademark Office*